(12) United States Patent  (10) Patent No.: US 9,035,122 B2
Richard  (45) Date of Patent: May 19, 2015

(54) WOUND DRESSING INHIBITING LATERAL DIFFUSION OF ABSORBED EXUDATE

(71) Applicant: PolyRemedy, Inc., San Jose, CA (US)

(72) Inventor: David A. Richard, Shingle Springs, CA (US)

(73) Assignee: PolyRemedy, Inc., Castro Valley, CA (US)

( * ) Notice: Subject to any disclaimer, the term of this patent is extended or adjusted under 35 U.S.C. 154(b) by 158 days.

(21) Appl. No.: 13/780,741

(22) Filed: Feb. 28, 2013

(65) Prior Publication Data

US 2013/0231623 A1  Sep. 5, 2013

Related U.S. Application Data

(60) Provisional application No. 61/606,911, filed on Mar. 5, 2012.

(51) Int. Cl.
A61F 13/00 (2006.01)

(52) U.S. Cl.
CPC ..... *A61F 13/00042* (2013.01); *A61F 13/00987* (2013.01); *A61F 13/00029* (2013.01)

(58) Field of Classification Search
CPC ...................... A61F 13/00017; A61F 13/00029
See application file for complete search history.

(56) References Cited

U.S. PATENT DOCUMENTS

| 6,110,849 | A  | * | 8/2000 | Tsai et al. ................ 442/394 |
| 6,506,873 | B1 | * | 1/2003 | Ryan et al. ............... 528/354 |
| 6,897,349 | B2 | * | 5/2005 | Gibbins et al. ............ 602/48 |
| 2006/0020235 | A1 | | 1/2006 | Siniaguine |
| 2007/0018361 | A1 | | 1/2007 | Xu |
| 2007/0255193 | A1 | * | 11/2007 | Patel et al. ................ 602/48 |
| 2008/0167594 | A1 | | 7/2008 | Siniaguine |
| 2011/0208101 | A1 | * | 8/2011 | Keller et al. ............... 602/44 |
| 2012/0157945 | A1 | * | 6/2012 | Robinson et al. .......... 604/319 |
| 2012/0215193 | A1 | * | 8/2012 | Siniaguine et al. ........ 604/368 |
| 2013/0172843 | A1 | * | 7/2013 | Kurata ...................... 604/372 |
| 2014/0107555 | A1 | * | 4/2014 | Patel ......................... 602/48 |

OTHER PUBLICATIONS

Opinion on the safety of poly(hexamethylene) biguanide hydrochloride (PHMB), Scientific Committee on Consumer Safety, European Commission (Dec. 16, 2014).*
Patent Cooperation Treaty, International Search Report and Written Opinion, International Patent Application No. PCT/US2013/028706, May 9, 2013, 7 Pages.

* cited by examiner

*Primary Examiner* — Susan Su
(74) *Attorney, Agent, or Firm* — Fenwick & West LLP

(57) ABSTRACT

A wound dressing including a hydrophilic layer and a hydrophobic layer is described. The hydrophilic layer absorbs exudate from a wound and the hydrophobic layer absorbs the exudate from the hydrophilic layer and traps the exudate. Because the hydrophilic layer is used adjacent to the wound, the exudate is readily absorbed thereby reducing the risk of maceration and infection of the wound tissue by the exudate. The hydrophobic layer receives the absorbed exudate from the hydrophilic layer and traps the exudate through an interaction that in turn prevents lateral diffusion of the exudate through the bandage to healthy portions of the skin. The hydrophilic and hydrophobic layers are fabricated from polymer fibers that can be spun to include components that facilitate wound healing, such as poly(hexamethylene biguanide) and/or hyaluronic acid.

20 Claims, 3 Drawing Sheets

WOUND DRESSING INHIBITING LATERAL DIFFUSION OF ABSORBED EXUDATE

CROSS REFERENCE TO RELATED APPLICATIONS

This application claims the benefit of U.S. Provisional Application No. 61/606,911, filed Mar. 5, 2012, which is incorporated by reference in its entirety.

BACKGROUND

The disclosure relates to a wound dressing having a structure that absorbs exudate from a wound and inhibits lateral diffusion of the exudate within the wound dressing, thereby reducing the exposure of unwounded skin to exudate.

When skin is inflamed or wounded, areas of skin that are normally relatively dry may become unduly wet from the flow of liquid (exudate) discharged from the wound. The exudate from the wound can move over drier and/or healthier skin areas. Also, deeper parts of the skin structure that are normally wet and free of harmful microorganisms may become dry thereby risking infection from colonized bacteria due to exposure to open air and contaminants.

Conventional wound treatments apply a homogenous wound dressing (e.g., one made of woven cotton threads) over the entire wound area primarily for the purpose of keeping the wound clean, absorbing some initial bleeding, protecting it from external contaminants, and/or protecting it from direct physical trauma.

FIG. 1 is a sectional diagram of a conventional wound dressing 10. The conventional wound dressing 10 may be a gauze bandage or a multi-layer wicking bandage that wicks exudate from a wound approximately uniformly in all directions. As the conventional wound dressing 10 becomes saturated by exudate at some locations, the exudate diffuse laterally throughout the wound dressing. This lateral diffusion of exudate (as illustrated by arrows 14) to other regions of the wound dressing 10 can then cause contact between healthy portions 18 of the skin and the exudate. This is problematic because the exudate may be contaminated with bacteria or other harmful substances, thereby infecting or injuring otherwise healthy portions 18 of the skin.

Furthermore, the conventional wound dressing 10 can become an antagonist to the wound 16 by not only maintaining contact between the wound and a portion of the conventional dressing that is saturated with exudate, but also by adhering to healing portions of the wound. Upon removal of the conventional wound dressing 10, the healing portions of the wound 16 are disturbed, delaying healing and increasing the risk of scarring.

SUMMARY

Embodiments relate to a wound dressing including a hydrophilic layer that absorbs exudate from a wound and a hydrophobic layer that absorbs the exudate from the hydrophilic layer and traps the exudate. Because the hydrophilic layer is used adjacent to the wound, the exudate is absorbed thereby reducing the risk of maceration and infection of the wound tissue by the exudate. The hydrophobic layer receives the absorbed exudate from the hydrophilic layer and traps the exudate, which in turn prevents lateral diffusion of the exudate through the bandage to healthy portions of the skin. The hydrophilic and hydrophobic layers are fabricated from polymer fibers that can be spun to include components that facilitate wound healing.

In one embodiment, the second fibrous polymer of the hydrophobic layer undergoes a volume reduction upon storing the exudate at inter-fiber gaps.

In one embodiment, the first fibrous polymer of the proximal hydrophilic layer comprises fibers of poly(ethylene-co-vinyl alcohol), the fibers having an average diameter of about 180 nm to about 400 nm.

In one embodiment, the first fibrous polymer of the proximal hydrophilic layer further comprises poly(hexamethylene biguanide) in the fibers of poly(ethylene-co-vinyl alcohol).

In one embodiment, the first fibrous polymer of the proximal hydrophilic layer comprises fibers of poly(ethylene oxide), the fibers having inter-fiber (interstitial) gaps of approximately 1 µm by 2.5 µm and fiber diameters of approximately 180 nm to 1.125 microns.

In one embodiment, the second fibrous polymer of the hydrophobic layer comprises fibers of poly(caprolactol), the fibers having an average diameter of about 180 nm to about 400 nm.

In one embodiment, the second fibrous polymer of the hydrophobic layer further comprises fibers of poly(caprolactol) mixed with the fibers of poly(hexamethylene biguanide).

In one embodiment the second fibrous polymer of the hydrophobic layer comprises fibers of poly(caprolactol), the fibers having an interstitial gap size of approximately 1 µm by 2.5 µm.

In one embodiment, the second fibrous polymer of the hydrophobic layer further comprises poly(hexamethylene biguanide) in the fibers of poly(caprolactol).

In one embodiment, a distal hydrophilic layer is in contact with the hydrophobic layer opposite the proximal hydrophobic layer, the distal hydrophilic layer facilitating evaporation of liquid in the exudate from the wound dressing.

In one embodiment, the hydrophobic layer includes at least a first and a second hydrophobic sub-layer, the first hydrophobic sub-layer including fibers of poly(caprolactol) ("PCL"), hyaluronic acid ("HA"), a tri-block copolymer of poly(ethylene glycol) and poly(propylene glycol) ("Poloxamer 188" (poly(ethylene glycol)-block-poly(propylene glycol)-block-poly(ethylene glycol), and sodium chloride("NaCl"). These fibers can also include varying amounts of (poly (hexamethylene biguanide hydrochloride)) ("PHMB"). A second hydrophobic sub-layer can include fibers of PEO (polyethylene oxide) and PCL (poly-caprolcatol) forming a matrix.

Embodiments also relate to a method for producing a wound dressing material. A voltage difference is applied between a rotating drum of an electro-spinner and at least one spinneret. A hydrophilic polymer solution is provided to the rotating drum through the at least one spinneret to fabricate a fibrous proximal hydrophilic layer of the wound dressing material on the rotating drum. A hydrophobic polymer solution is provided to the rotating drum through the at least one spinneret to fabricate a fibrous hydrophobic layer in contact with the proximal hydrophilic layer. The fibrous hydrophobic layer includes inter-fiber gaps for receiving exudate from a wound via the fibrous proximal hydrophilic layer when a portion of the wound dressing material is placed on the wound. The fibrous hydrophobic layer inhibits lateral diffusion of the exudate within the wound dressing material.

In one embodiment, the hydrophilic polymer solution has a viscosity of between 200 centiPoise and 400 centiPoise.

In one embodiment, the hydrophobic polymer solution has a viscosity of between 200 centiPoise and 400 centiPoise.

In one embodiment, the fibrous proximal hydrophilic layer comprises fibers having a diameter of between 180 nm and 400 nm.

In one embodiment, the fibrous hydrophobic layer comprises fibers having a diameter of between 180 nm and 400 nm.

In one embodiment, the method further includes adding hyaluronic acid to the hydrophilic polymer solution before providing the hydrophilic polymer solution to the rotating drum.

In one embodiment, the method further includes adding hyaluronic acid to the hydrophobic polymer solution before providing the hydrophobic polymer solution to the rotating drum.

In one embodiment, the method further includes the fibrous hydrophobic layer having interstitial gaps with a size of 1 μm by 2.5 μm In one embodiment, the method further includes placing an occlusive film on the rotating drum before providing the hydrophilic polymer solution to the rotating drum.

The figures depict various embodiments for purposes of illustration only. One skilled in the art will readily recognize from the following discussion that alternative embodiments of the structures and methods illustrated herein may be employed without departing from the principles described herein.

DETAILED DESCRIPTION

Embodiments relate to a wound dressing that does not merely absorb exudate from a wound, but rather traps the exudate in gaps between hydrophobic fibers in the wound dressing. This trapping prevents lateral diffusion of the exudate through the bandage to healthy portions of the skin, thereby reducing the exposure of healthy skin to exudate and lowering the risk of maceration or infection of the healthy skin. Material of a wound dressing may be fabricated by providing solutions of a hydrophobic polymer and a hydrophilic polymer to a rotating drum of an electro-spinner.

Figure 2:
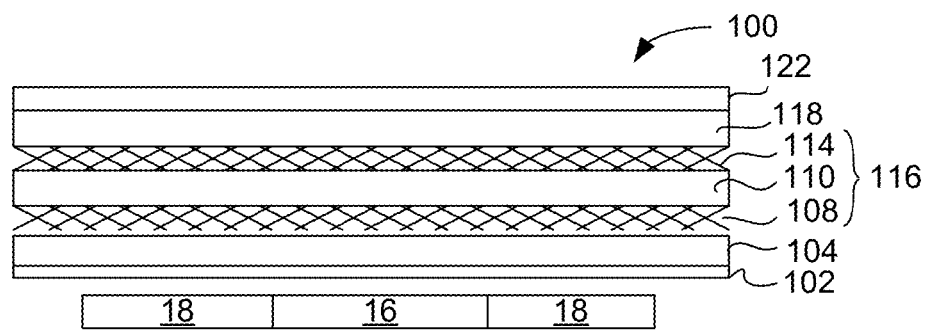
FIG. 2 is a cross-sectional diagram of a wound dressing structured to prevent lateral diffusion of exudate, according to one embodiment.

FIG. 2 is a sectional diagram of a wound dressing 100, according to one embodiment. The wound dressing 100 absorbs and traps exudate, thereby preventing the exudate from contacting healthy skin or at least reducing the exposure of healthy skin to the exudate compared to conventional wound dressings. The wound dressing 100 may include, among other layers, a proximal hydrophilic layer 104, a hydrophobic layer 116, a distal hydrophilic layer 118 and a protective layer 122. The proximal hydrophilic layer 104 may be coated with a medicine or a substance 102 beneficial to healing of a wound (e.g., mineral oil). The wound dressing 100 may also include other layers not illustrated in FIG. 2.

The proximal hydrophilic layer 104 absorbs exudate from the wound and provides the exudate to the hydrophobic layer 116. Because the proximal hydrophilic layer 104 includes hydrophilic polymers, the exudate is readily absorbed thereby reducing the residence time of the exudate in the wound. This in turn reduces the risk of maceration of the wound tissue by the exudate and also reduces the risk of infection by bacterially contaminated exudate.

In one embodiment, the proximal hydrophilic layer 104 is made of poly(ethylene-co-vinyl-alcohol) ("EVOH" having a mer chemical composition of ($CH_2CHOH$)). In this embodiment, the vinyl alcohol groups provide the hydrophilicity of the proximal hydrophilic layer 104, although any hydrophilic polymer capable of being spun or fabricated into a fibrous structure can also be used. Alternative hydrophilic polymers can also be used in the proximal hydrophilic layer 104.

In another embodiment, the hydrophilic polymer used in the proximal hydrophilic layer 104 is embedded with poly(hexamethylene biguanide hydrochloride) ("PHMB" having a mer chemical composition of ($C_8H_{17}N_5$)). In this embodiment, PHMB is spun into the proximal hydrophilic layer 104 as described below in FIG. 3, thereby becoming a component of the fibers forming the hydrophilic polymer and preventing and/or suppressing growth of bacteria in the exudate within the wound dressing 100. Other similar anti-bacterial additives can be used in the wound dressing 100, whether incorporated into the polymer fibers of the wound dressing 100 or otherwise applied to or mixed with the fibers. Examples of alternative anti-bacterial additives include silver, and polyamineopropinol biguanide.

Figure 3:
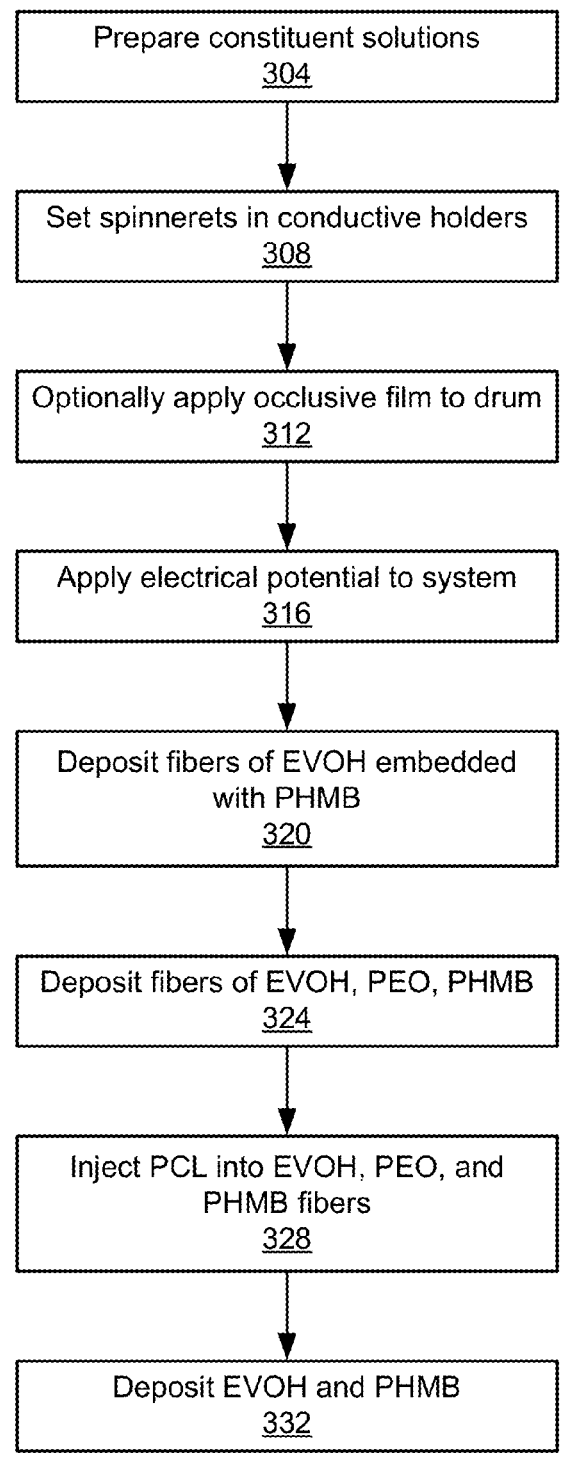
FIG. 3 is a flowchart illustrating a process of fabricating a wound dressing, according to one embodiment.

Similarly, hyaluronic acid can be added as a component of the fibers of the proximal hydrophilic layer 104 as described in method 300 in FIG. 3. "Hyaluronic acid" includes the corresponding metal salts of hyaluronic acid, including, for example, sodium hyaluronate (the sodium salt), potassium hyaluronate, zinc hyaluronate, magnesium hyaluronate, and calcium hyaluronate (generally known as hyaluronic acid). By incorporating hyaluronic acid into the fibers of the proximal hydrophilic layer 104 (and/or into the fibers of the hydrophobic layer 116), the hyaluronic acid can be provided to the wound in a controlled way, thereby facilitating healing and reducing scarring by displacing collagen at the wound. The wound dressing 100 releases hyaluronic acid in a controlled way as exudate is absorbed into the wound dressing. That is, as exudate is absorbed by the wound dressing 100, the exudate displaces hyaluronic acid in the fibers of the wound dressing 100, thereby allowing the dressing 100 to provide the hyaluronic acid to the wound progressively as exudate is received by the dressing. This, unlike conventional applications of hyaluronic acid where a bulk application is used, does not flood or occlude the wound with hyaluronic acid, which can slow healing.

Furthermore, the inclusion of hyaluronic acid in fibers of the dressing increases the tensile strength of the EVOH fibers. In some examples, up to 50 wt. %/wt. % of hyaluronic acid is added to the PCL. In addition to the beneficial healing effects, the mechanical properties and durability of the proximal hydrophilic layer 104 are further improved. After exudate is absorbed by the proximal hydrophilic layer 104, the hydrophobic layer 116 can absorb the exudate from the proximal hydrophilic layer and trap the exudate in inter-fiber gaps with minimal, if any, lateral diffusion of the exudate in either the proximal hydrophilic layer 104 or in the hydrophobic layer 116. It may be that the exudate is trapped in the inter-fiber gaps through an electrochemical interaction between at least some of the exudate and the hydrophobic polymer fibers. Surface tension or other similar forces may also contribute to trapping exudate in these gaps. Regardless of the mechanism, this attraction between the fibers of the dressing 100 and model exudate has been observed using an optical microscope at a magnification of approximately 100× by placing a fiber proximate to the exudate and observing the flexure of the fiber toward the exudate.

Because exudate is trapped in gaps between the polymer fibers, the lateral diffusion of the exudate from the wound 16 to healthy portions of skin 18 is significantly reduced. The model exudate used in this case had a composition of sodium chloride and calcium chloride containing 142 mmol/liter of sodium ions and 2.5 mmol/liter of calcium ions, which are values typical found in serum and wound fluid. Model exudate is used to mimic a standard wound pH (pH 6.7-7.9). It will be appreciated that this composition is only one of an infinite variety of exudate that can be produced by a wound.

One benefit of selecting a polymer having an interaction with exudate is that the polymer fibers are drawn toward each other as the inter-fiber gaps are filled with exudate. This phenomenon can cause up to approximately a 20% reduction in the volume of the wound dressing 100, thereby reducing pressure on the wound and preventing further irritation of the wound by the wound dressing.

The hydrophobic layer 116 in this embodiment can be fabricated by electro-spinning and/or producing fibers of the poly(caprolactol) ("PCL") that are embedded with PHMB. These fibers can also be combined with electrospun fibers of EVOH embedded with PHMB (in a concentration of from about 0.2% through about 0.5% for antimicrobial effect) and can also be combined with fibers of poloxamer (a tri-block copolymer having a central hydrophobic segment (e.g., poly (propylene oxide) surrounded by terminal hydrophilic segments (e.g., poly(ethylene oxide) or "PEO"), such as P188. The PEO and EVOH fibers can be combined with PCL having a mer chemical composition of $(C_6H_{10}O_2)$. An example method of fabrication is described in more detail in FIG. 3.

One of many benefits of combining PEO and/or EVOH fibers with PCL fibers is that the mechanical integrity of the wound dressing 100 is improved because the PCL fibers have a higher modulus and a higher tensile strength than PEO and EVOH. This allows for removal of the wound dressing 100 from the wound in a single piece without leaving fragments of the wound dressing in the wound and helps reduce the risk of infection and/or scarring of the wound. Improved mechanical integrity also allows for improved handling of the dressing because the dressing 100 is not damaged by routine handling. Another benefit of combining fibers in this way is that the creation of interstitial (and in this example repository) gaps between the fibers in the hydrophobic layer 116 (which can trap exudate as described above) is facilitated. These intersitital gaps have approximate volumes of between 1 cubic micron and 2 cubic microns. A benefit of combining PCL fibers with EVOH fibers in the hydrophobic layer 116 is that the combination facilitates moisture vapor transmission via the gaps between the fibers in the layer. This can improve oxygen transport to the skin through the dressing 100 and can reduce the amount of exudate in the dressing. One alternative to PCL used to improve the structural integrity of the wound dressing 100 is hyaluronic acid. When incorporated into the polymer fibers, the hyaluronic acid increases the tensile strength of the fibers, thereby improving the structural integrity of the wound dressing 100.

In the embodiment of the wound dressing 100 shown in FIG. 2, the hydrophobic layer 116 includes multiple sub-layers including an inner sub-layer 108, a middle sub-layer 110 and an outer sub-layer 114. In the embodiment shown, the inner sub-layer 108 and the outer sub-layer 114 include higher concentrations of PCL and a lower concentration of PEO/PHMB relative to the middle sub-layer 110. The higher concentration of PEO in the middle sub-layer 110 allows for the middle sub-layer to store the bulk of exudate from a wound, whereas the lower concentration of PEO at the inner and outer sub-layers 108 and 114 allows for vapor transport of the exudate to the middle sub-layer 110 from the proximal hydrophilic layer 104 and from the middle sub-layer 110 to the air.

Figure 1:
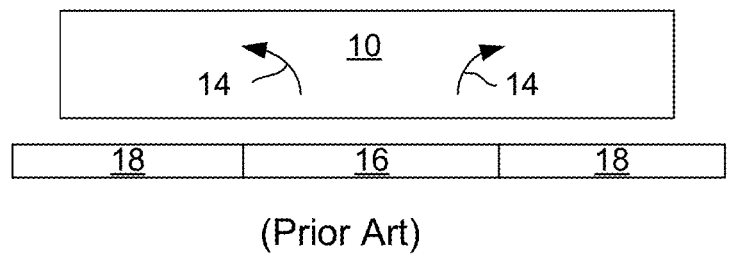
FIG. 1 is a cross-sectional diagram of a conventional wound dressing.

While the foregoing discussion and FIGS. 1 and 2 refer to "layers" of the wound dressing 100, the use of this term and the depiction in FIG. 2 of well-defined boundaries is for convenience and clarity of explanation. The boundaries between these layers are not as well defined as shown in FIG. 2, but rather transition from one composition to another as a function of the electro-spinning process used to fabricate the dressing 100.

The foregoing discussion also refers to various example polymers convenient for preventing the migration of exudate from the wound to healthy portions of skin. In addition to the hydrophilicity and hydrophobicity of the example polymers presented above, another factor in the selection of polymers for use in the wound dressing 100 is the stability of a polymer at various pH values. For example, the pH of an acute wound at hemostasis is approximately 6.2. The wound becomes more acidic during the inflammatory stage of wound healing, steadily increasing during granulation and returning an approximately neutral pH during the final stages of re-epithelialization. The pH of chronic wounds arrested in the inflammatory stage of wound healing average around 7.5 with considerable variation. Therefore, depending on the type of wound and the intended use of the dressing, pH of the wound during healing may be included as one factor used for selecting a polymer for the wound dressing 100.

The wound dressing 100 may further include a distal hydrophilic layer 118. The distal hydrophilic layer 118 may be made of a combination of PEO, EVOH, and PHMB. In some examples, the distal hydrophilic layer 118 can be placed adjacent to the wound 16 instead of the proximal hydrophilic layer 104. That is, the symmetric configuration of the wound dressing 100 allows either the proximal or the distal hydrophilic layer to come in contact with the wound without altering the function of the wound dressing. Furthermore, the wound dressing 100 may also include a surface protective layer 122 made of a thermoplastic (such as poly(urethane)) that can be either non-occlusive or semi-occlusive depending on thickness.

FIG. 3 is a flowchart illustrating a process 300 for fabricating the wound dressing 100, according to one embodiment. In this embodiment, the hydrophilic layers 118, 104 and the hydrophobic layer 116 are fabricated using an electro-spinning process.

Solutions of the polymers used to form the wound dressing 100 are prepared 304 by dissolving the desired polymers in a solvent appropriate for electro-spinning. For example, EVOH, and PCL can be dissolved in ethyl alcohol, methyl alcohol, chloroform, or combinations thereof. The concentration of the solution can be varied to achieve a viscosity of the solution (which is dependent on the molecular weight of the polymer and the strength of the solvent) appropriate to the electro-spinning voltage and device configuration, but solutions typically have a concentration of between 10 wt. % and 20 wt. %.

As described above, PHMB can be dissolved in the constituent solution for the proximal hydrophilic layer 104 and/or the hydrophobic layer 116 to provide an anti-microbial effect to the wound dressing 100. Similarly, hyaluronic acid can also be added to one or more constituent solutions used to produce fibers that include hyaluronic acid, the fibers thereby releasing the acid to the wound as the exudate is absorbed, as described above in the context of FIG. 2. Mineral oil may also be dissolved in a constituent solution as another supplement that can enhance healing of the wound.

Up to about 0.06 wt. % of NaCl is added to the constituent solutions along with 0.5 wt. % of a poloxamer, such as P188 (i.e., having a molecular weight of 18,000 g/mol, and being 80% poly(oxyethylene)). The addition of the NaCl and the poloxamer facilitate the electro-spinning of the constituent solutions at even relatively low viscosities. For example, upon addition of these components, the viscosities of the constituent solutions can be as low as 200 to 400 centiPoise. A benefit of using solutions at this low viscosity for electro-spinning is that fibers with nano-scale diameters (e.g., at or less than about 180 nm) can be achieved using otherwise conventional electro-spinning methods.

To create a jet of the constituent solutions that ultimately forms the polymer fibers of the wound dressing 100, spinnerets are set 308 in conductive holders around a conductive drum. The conductive drum can have a diameter of between 200 cm and 500 cm and is placed between 10 cm and 20 cm away from the spinnerets. This configuration is used to spin fibers from the constituent solutions as described herein. In this example, the inner diameter of the outlet port of a spinneret is approximately 0.06 cm in diameter, but can be bigger or smaller depending on the constituent solution concentration and the desired fiber diameter. Prior to fabricating the fibers from solution, an occlusive film (e.g., polyurethane film) may optionally be applied 312 to the drum prior to the electro-spinning deposition of the fibers. The occlusive film can be used as some, or all, of the protective layer 122 of the wound dressing 100.

An electrical potential of from about 25 kV to about 40 kV is applied 316 to the conductive solutions and the conductive drum, thereby creating an electric field at a tip of the spinnerets (also known as "capillary tubes"). As a result of this electric field, the surface of the fluid at the tips of the spinnerets elongates to form a conical shape known as a Taylor Cone. As the electrical field is increased, the repulsive electrostatic force overcomes the surface tension of the solution within the capillary tube and a jet of fluid is ejected from the Taylor Cone at the tip of the capillary tube. The discharged polymer solution jet, flowing at a rate of between 10 milliliters/hour and 30 milliliters/hour undergoes a whipping process in the zone between the cone and the drum where the solvent evaporates leaving behind a fiber that lays itself randomly on the rotating metal drum and forms the fiber matrix material from which the wound dressing is made 100.

The concentration of the constituent solutions and/or the flow rate of the solutions from the spinnerets can be controlled to spin fibers of a desired diameter. For example, solutions having a concentration of from about 2 wt. % to about 12 wt. % of polymer (the polymer having a molecular weight of about 200,000 g/mol) in solvent and flowed through a spinneret from about 0.2 milliliters/min to about 0.5 milliliters/min can be used to produce fibers having an approximate diameter from about 100 nm to about 2200 nm. In general, the smaller the diameter of the fiber, the more hydrophobic the fiber as indicated by a water contact angle measurement. For example, fibers produced according to the method 300 having an average diameter of about 2200 nm exhibit a (water) contact angle of about 120°, whereas fibers having an average diameter of about 600 nm exhibit a contact angle of about 125°. For fibers having average diameters of less than approximately 600 nm, the contact angle exhibited, and therefore the surface energy, increases at a higher rate. For example, fibers having an average diameter of approximately 400 nm to approximately 180 nm exhibit contact angles of between approximately 130° to about 150° respectively. A higher surface energy of the fibers is beneficial for trapping exudates at inter-fiber gaps.

In one example, a solution of PEO, EVOH, and PHMB is deposited 320 as spun fibers on the drum, thereby forming the distal hydrophilic layer 118 fibers on the optional occlusive film placed the rotating drum. Subsequently, a solution including EVOH, PEO and PHMB is deposited 324 as fibers at the same time a PCL solution is injected 328 to deposit the hydrophobic layer 116 onto distal hydrophilic layer 118. The injection rate of PCL and PEO/PHMB may be varied during this step to form three sub-layers 108, 110, 114 of different PCT and PEO/PHMB weight or volume fractions, as described above.

Then a solution including PEO, EVOH, and PHMB is deposited 332 on the drum as spun fibers to form the proximal hydrophilic layer 104 on the injected hydrophobic layer 116. Mineral oil or other substance can then optionally be applied to the hydrophilic layer to form the layer 102. The wound dressing 100 can then be removed from the drum.

Figure 4A:
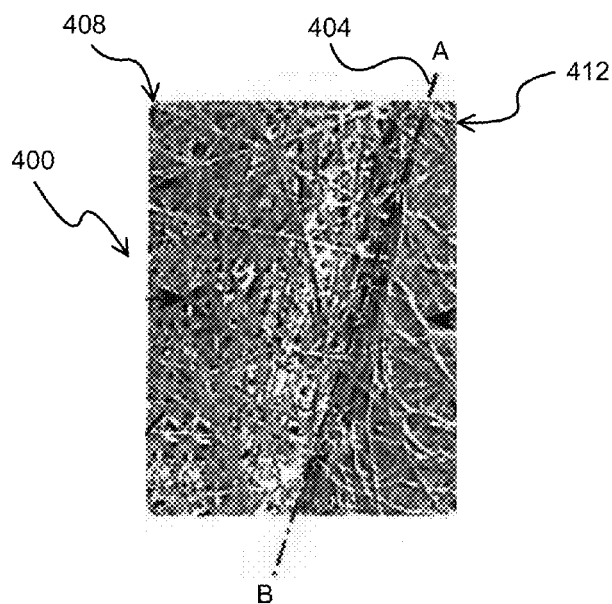
FIGS. 4A, 4B, and 4C are photo-micrographs illustrating experimental results of fibers at different portions of the wound dressing and at different stages of exudate absorption, according to one embodiment.
Figure 4B:
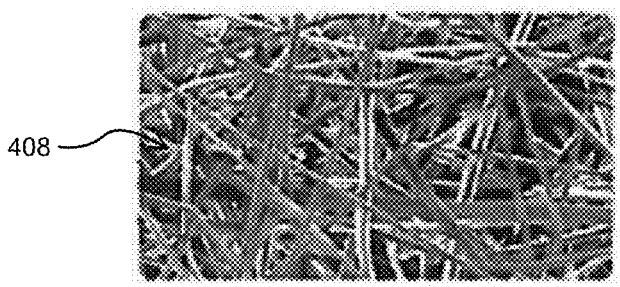
Figure 4C:
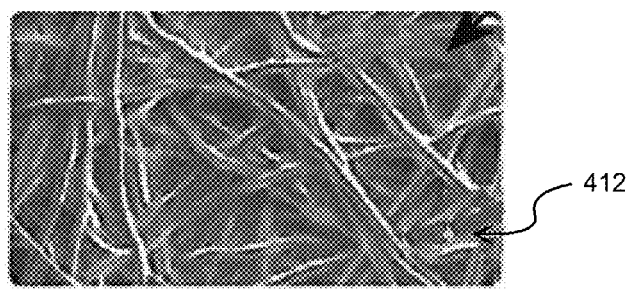

FIGS. 4A, 4B, and 4C illustrate results from an experiment of fabricating and using the wound dressing 100 described above. FIG. 4A is a photograph of a section of a wound dressing prepared using the method 300. Specifically, the wound dressing shown in FIG. 4A was prepared by first preparing a 15 wt. % solution of the foregoing polymers and additives in a mixture of chloroform and methanol. In this example, the PEO and PCL each have molecular weights of about 200,000 g/mol. The PEO further includes 27 mol. % of EVOH. The solutions included approximately 0.06 wt. % of NaCl and 0.5 wt. % of poloxamer P188.

The constituent solutions were placed in spinnerets having an outlet inner-diameter of 0.06 cm and an outlet outer-diameter of 0.09 cm. The solution was delivered through the spinnerets to a rotating drum at a rate of approximately 0.5 milliliters/minute and at a voltage of from about 20 kV to about 40 kV. The drum was rotated to produce a wound dressing 100 as described above having inter-fiber gaps used to trap exudate.

The wound dressing 100 was exposed to a sample exudate solution of sodium/calcium chloride containing 142 mmol/liter of sodium ions and 2.5 mmol/liter of calcium ions. These values are typical of those found in serum and wound fluid. Solutions in this compositional range are established to meet a standard wound pH (pH 6.7-7.9). This exudate was used merely for convenience and, as mentioned above, the variety of exudate compositions is nearly infinite, being a function of at least, an individual's body chemistry, wound type, and other factors.

After exposure to exudate, the micrograph 400 was captured at a magnification of 100× using scanning electron microscope. To the left of line A-B 404 is a region 408 of the wound dressing 400 unexposed to exudate either directly (by physical contact with the exudates at its source) or indirectly (as absorbed by and transported through the wound dressing). To the right of line A-B 404 is a region 412 exposed to exudate that has been absorbed. The conditions under which this exposure was performed are described above.

FIGS. 4B and 4C are 1000× magnifications of regions 408 and 412 respectively. As shown in FIGS. 4B and 4C and described above in the context of FIG. 2, the hydrophobic layer 116 retained exudate in the inter-fiber gaps of the wound dressing shown. This is unlike the unexposed region 408, in which the inter-fiber gaps remained empty of exudate. This phenomenon inhibited lateral diffusion of the exudate within the wound dressing and also reduced the volume of the wound dressing by approximately 20%.

While particular embodiments and applications have been illustrated and described, it is to be understood that the disclosed embodiments are not limited to the precise construction and components disclosed herein. Various modifications, changes and variations, which will be apparent to those skilled in the art, may be made in the arrangement, operation and details of the method and apparatus disclosed herein without departing from the spirit and scope defined in the appended claims.

What is claimed is:

1. A wound dressing comprising:
   a proximal hydrophilic layer fabricated from a first fibrous polymer including fibers that comprise at least one polymer and hyaluronic acid, the first fibrous polymer configured for placement adjacent to a portion of skin producing exudate to absorb the exudate; and
   a hydrophobic layer in contact with the proximal hydrophilic layer, the hydrophobic layer comprising a second fibrous polymer configured for receiving the exudate absorbed by the proximal hydrophilic layer and storing the exudate at inter-fiber gaps to inhibit lateral diffusion of the exudate in the wound dressing.

2. The wound dressing of claim 1, wherein the second fibrous polymer of the hydrophobic layer undergoes a volume reduction upon storing the exudate at interstitial gaps.

3. The wound dressing of claim 1, wherein the first fibrous polymer of the proximal hydrophilic layer comprises fibers of poly(ethylene oxide) and poly(ethylene-co-vinyl alcohol), the fibers having an average diameter of about 180 nm to about 400nm.

4. The wound dressing of claim 3, wherein the first fibrous polymer of the proximal hydrophilic layer further comprises poly(hexamethylene biguanide) in the fibers of poly(ethylene-co-vinyl alcohol).

5. The wound dressing of claim 1, wherein the first fibrous polymer of the proximal hydrophilic layer comprises fibers of poly(ethylene oxide) and poly(ethylene-co-vinyl alcohol), the fibers having an interstitial gap size of between 1 micron and 2.5microns.

6. The wound dressing of claim 1, wherein the second fibrous polymer of the hydrophobic layer comprises fibers of poly(caprolactol), the fibers having an average diameter of about 180 nm to about 400 nm.

7. The wound dressing of claim 6, wherein the second fibrous polymer of the hydrophobic layer further comprises fibers of poly(ethylene-co-vinyl alcohol) mixed with the fibers of poly(caprolactol).

8. The wound dressing of claim 1, wherein the second fibrous polymer of the hydrophobic layer comprises fibers of poly(caprolactol), the fibers having an interstitial gap size of between 1 micron and 2.5 microns.

9. The wound dressing of claim 1, wherein the second fibrous polymer of the hydrophobic layer further comprises poly(hexamethylene biguanide hydrochloride) in the fibers of poly(caprolactol).

10. The wound dressing of claim 1, further comprising a distal hydrophilic layer in contact with the hydrophobic layer and opposite the proximal hydrophilic layer, the distal hydrophilic layer facilitating evaporation of liquid in the exudate from the wound dressing.

11. The wound dressing of claim 1, wherein the hydrophobic layer includes at least a first and a second hydrophobic sub-layers, the first hydrophobic sub-layer comprising fibers of poly(caprolactol) that include hyaluronic acid, sodium chloride, and a tri-block copolymer of poly(ethylene glycol) and polypropylene glycol), and the second hydrophobic sub-layer comprising fibers poly(ethylene oxide) and poly(caprolactol).

12. The wound dressing of claim 1, wherein the fibers of the first fibrous polymer are configured to release hyaluronic acid as exudate is absorbed.

13. A wound dressing comprising:
   a proximal hydrophilic layer fabricated from a fibrous polymer and configured for placement adjacent to a portion of skin producing exudate to absorb the exudate; and
   a fibrous hydrophobic layer in contact with the proximal hydrophilic layer, the fibrous hydrophobic layer configured to receive the exudate absorbed by the proximal hydrophilic layer and store the exudate at inter-fiber gaps to inhibit lateral diffusion of the exudate in the wound dressing, the fibrous hydrophobic layer comprising:
      a first hydrophobic sub-layer comprising fibers of poly(caprolactol) that include hyaluronic acid, sodium chloride, and a tri-block copolymer of poly(ethylene glycol) and polypropylene glycol); and
      a second hydrophobic sub-layer comprising fibers poly(ethylene oxide) and poly(caprolactol).

14. The wound dressing of claim 13, wherein a volume of the fibrous hydrophobic layer is reduced as the exudate is stored at interstitial gaps of the fibrous hydrophobic layer.

15. The wound dressing of claim 13, wherein the fibers of poly(caprolactol) of the first hydrophobic sub-layer further comprise poly(hexamethylene biguanide hydrochloride) in the fibers of poly(caprolactol).

16. The wound dressing of claim 13, wherein the fibers of poly(caprolactol) of the first hydrophobic sub-layer have an interstitial gap size of between 1 micron and 2.5 microns.

17. The wound dressing of claim 13, wherein the proximal hydrophilic layer comprises fibers of poly(ethylene oxide) and poly(ethylene-co-vinyl alcohol), the fibers having an interstitial gap size of between 1 micron and 2.5 microns.

18. The wound dressing of claim 13 wherein the fibrous polymer of the proximal hydrophilic layer comprises poly(hexamethylene biguanide) in fibers of poly(ethylene-co-vinyl alcohol).

19. The wound dressing of claim 13, further comprising a distal hydrophilic layer in contact with the fibrous hydrophobic layer and locate opposite to the proximal hydrophilic layer, the distal hydrophilic layer configured to facilitate evaporation of liquid in the exudate from the wound dressing.

20. A wound dressing comprising:
   a proximal hydrophilic layer fabricated from a first fibrous polymer and configured for placement adjacent to a portion of skin producing exudate to absorb the exudate; and
   a hydrophobic layer in contact with the proximal hydrophilic layer, the hydrophobic layer comprising a second fibrous polymer of poly(caprolactol) having a plurality of interstitial gaps, each interstitial gap having a size of between 1 micron and 2.5microns, the second fibrous polymer configured for receiving the exudate absorbed by the proximal hydrophilic layer and storing the exudate at the plurality of interstitial gaps to inhibit lateral diffusion of the exudate in the wound dressing.

* * * * *